(12) United States Patent
Lu et al.

(10) Patent No.: US 9,006,402 B2
(45) Date of Patent: Apr. 14, 2015

(54) QUATERNARY DATA-STORAGE MATERIALS AND THE PREPARATION METHOD THEREOF

(71) Applicant: Soochow University, Suzhou (CN)

(72) Inventors: Jian-Mei Lu, Suzhou (CN); Hua Li, Suzhou (CN)

(73) Assignee: Zhangjiagang Institute of Industrial Technologies Soochow University, Zhangjiagang, Jiangsu Province (CN)

( * ) Notice: Subject to any disclaimer, the term of this patent is extended or adjusted under 35 U.S.C. 154(b) by 373 days.

(21) Appl. No.: 13/712,280

(22) Filed: Dec. 12, 2012

(65) Prior Publication Data
US 2014/0085771 A1    Mar. 27, 2014

(51) Int. Cl.
| | | |
|---|---|---|
| C09B 35/037 | (2006.01) | |
| G11C 13/02 | (2006.01) | |
| C07C 317/34 | (2006.01) | |
| C07C 315/04 | (2006.01) | |
| H01G 4/018 | (2006.01) | |
| H01G 4/33 | (2006.01) | |
| H01G 4/18 | (2006.01) | |
| G11C 11/56 | (2006.01) | |
| G11C 13/00 | (2006.01) | |
| H01L 51/05 | (2006.01) | |

(52) U.S. Cl.
CPC ............. *C07C 317/34* (2013.01); *C07C 315/04* (2013.01); *H01G 4/018* (2013.01); *C09B 35/037* (2013.01); *H01G 4/33* (2013.01); *H01G 4/18* (2013.01); *H01L 51/0595* (2013.01); *G11C 11/5664* (2013.01); *G11C 13/0014* (2013.01)

(58) Field of Classification Search
CPC .......................... C09B 35/037; G11C 13/0014
USPC .......................................... 534/821; 365/151
See application file for complete search history.

(56) References Cited

FOREIGN PATENT DOCUMENTS

CN    101665678    *  3/2013   ............... C09K 3/00

OTHER PUBLICATIONS

Nunzi et al. (Proceedings of 2001 3rd International Conference on Transparent Optical Networks, 2001, pp. 135-138).*
Li, Hua et al., "A Small-Molecule-Based Ternary Data-Storage Device", J. AM. Chemical Society, 2010, 132, pp. 5542-5543.
Jung, Yeonwoong et al., "Core-Shell Heterostructured Phase Change Nanowire Multistate Memory", NANO Letters, 2008, vol. 8, No. 7, pp. 2056-2062.

* cited by examiner

*Primary Examiner* — Robert Havlin
(74) *Attorney, Agent, or Firm* — McKenna Long & Aldridge LLP

(57) ABSTRACT

An organic compound has the following chemical structure:

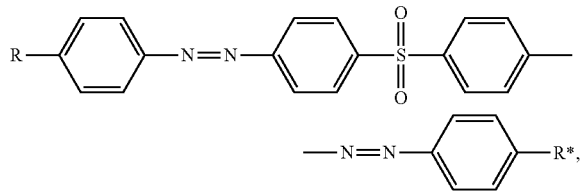

wherein R is different from R*; R and R* are independently hydrogen,

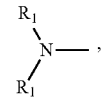

halogen, nitro or methoxyl; and R1 is a C1-C6 alkyl or a phenyl group. A quaternary data storage device includes a bottom electrode, a top electrode, and the organic film layer sandwiched between the bottom electrode and the top electrode.

16 Claims, 2 Drawing Sheets

QUATERNARY DATA-STORAGE MATERIALS AND THE PREPARATION METHOD THEREOF

The present invention claims priority to Chinese Patent Application No. 201104448530, filed on Dec. 27, 2011.

BACKGROUND OF THE INVENTION

1. Field of the Invention

The present invention relates to an organic compound, a quaternary data storage device containing the organic compound, and a method of preparing the organic compound and the quaternary data storage device.

2. Discussion of the Related Art

At the end of 2009, the movie Avatar with the 3D Imax technique won a wide reputation around the globe due to the unprecedented enjoyment it brought visually and acoustically. However, the film of this movie weighs up to 700 kilograms, indicating that the current memory materials and techniques are far behind the pace of the rapid development of the information society. Till now, almost all the efforts in the high density data storage field are focused on increasing the data storage density via diminishing the scale of the memory cells. When inorganic material suffered its bottleneck due to its intrinsic properties to further diminish the scale, researchers have turned their attention to polymeric and organic materials possessing good processability with the anticipation that the data storage density could be further enhanced by diminishing the scale of the memory units. The scale can only be diminished from the microscale to nanoscale with the storage density increase no more than 1000 times, which also cannot meet the requirements for super-high density data storage in the long run. The reason is that current optical, magnetic and electric memories based on polymeric and organic materials are generally conventional binary memory ("0" and "1"). To further enhance the data storage density, researchers successively achieved ternary storage ("0", "1", "2") with inorganic nanowires and organic materials respectively, breaking through the conventional binary memory, dramatically increasing the storage density of unit area tens of thousands of times (i.e., for the same 40 storage units, the storage density for ternary memory is more than 10 million times higher than that for binary memory). See, e.g., H. Li, Q. Xu, N. Li, R. Sun, J. Ge, J. Lu, H. Gu, F. Yan, J. Am. Chem. Soc. 2010, 132, 5542; and Y. W. Jung, S. H. Lee, A. T. Jennings, R. Agarwal, Nano Lett. 2008, 8, 2056. In this way, enormous storage capacity can be attained with less storage units, making the storage cells more compact. And the fabricating process for the device can be simplified, thus achieving a new generation of super-high density data storage devices with high capacity, small dimension, low power consumption and low cost.

The data storage density can be further enhanced with continuing increase in the quantity of electrically stable states. Accordingly, there exists a need for new data storage materials with increased quantity of electrically stable states and data storage density.

SUMMARY OF THE INVENTION

In one embodiment of the present invention, an organic compound has the following chemical structure:

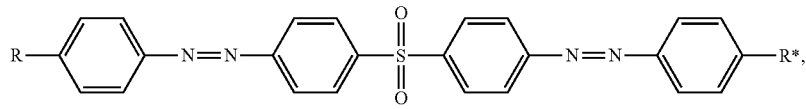

wherein R is different from R*; R and R* are independently hydrogen,

halogen, nitro or methoxyl; and R1 is a C1-C6 alkyl or a phenyl group.

In another embodiment of the present invention the organic compound is selected from the group consisting of

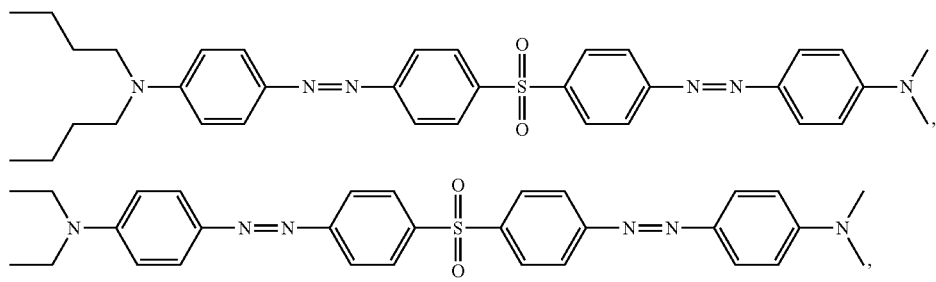

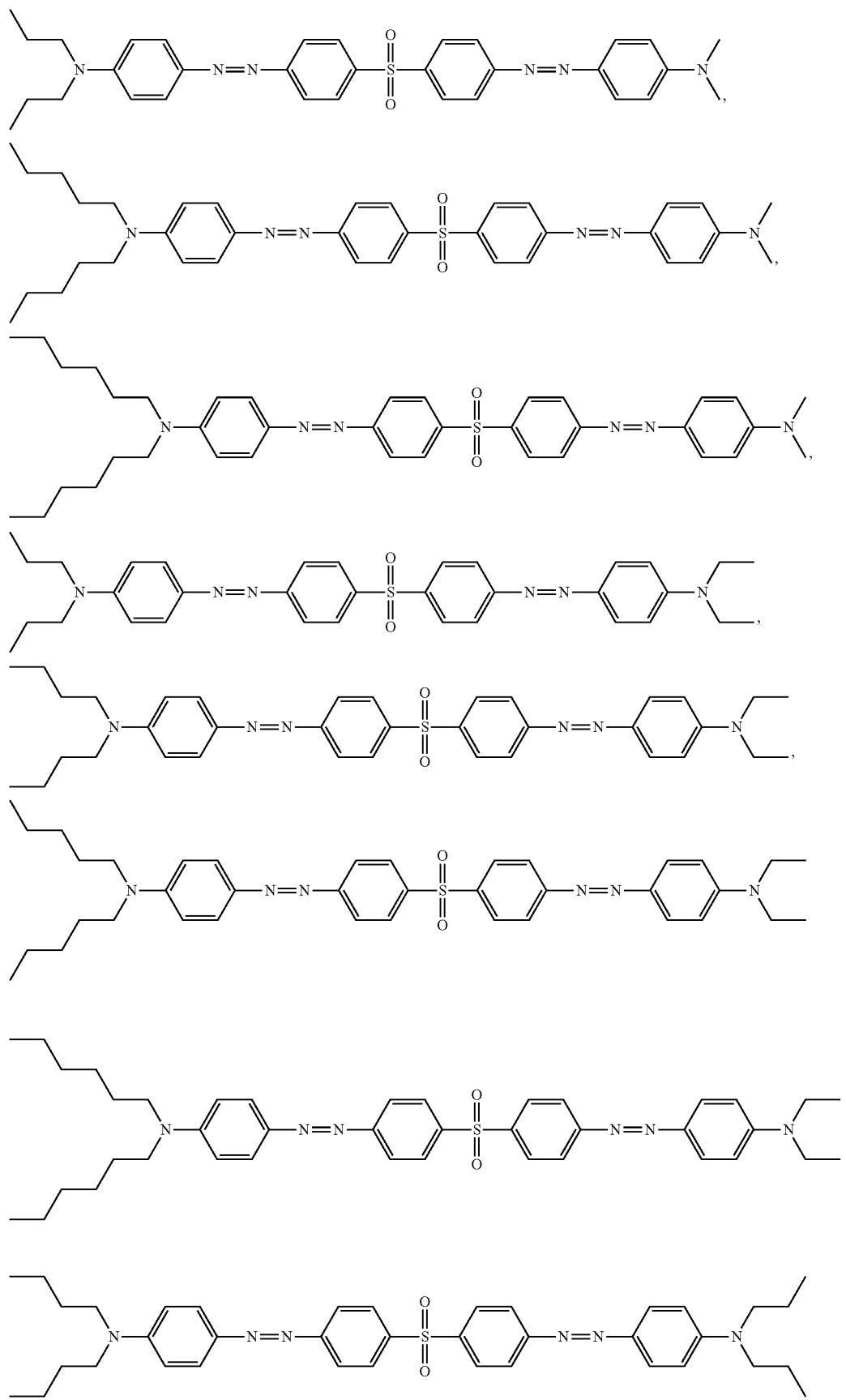

-continued

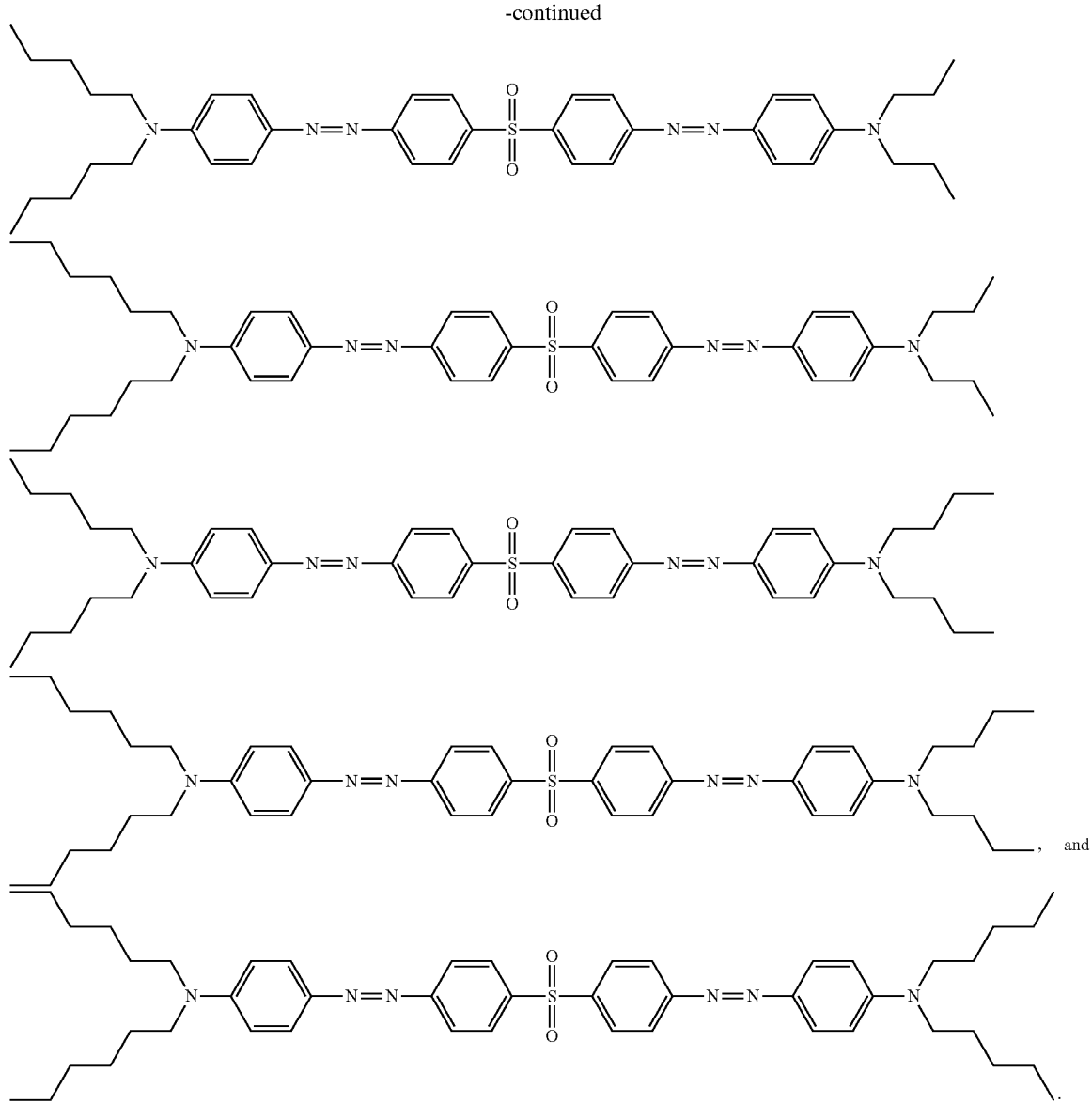
, and

In another embodiment of the present invention, a quaternary data storage device includes a bottom electrode, a top electrode, and an organic film layer sandwiched between the bottom electrode and the top electrode. The organic film layer contains the organic compound.

In another embodiment of the present invention, the thickness of the bottom electrode is 10-300 nm, the thickness of the top electrode is 20-300 nm, and the thickness of the organic layer is 20-150 nm.

In another embodiment of the present invention, the bottom electrode is selected from the group consisting of indium-tin oxide (ITO), an evaporatable metal, and a conductive polymer. The evaporatable metal can be gold, platinum, silver, aluminum, or copper; and the conductive polymer can be polythiophene or polyaniline.

In another embodiment of the present invention, the top electrode is selected from the group consisting of an evaporatable metal and a metal oxide. The evaporatable metal can be gold, platinum, silver, or copper; and the metal oxide can be indium-tin oxide (ITO).

In another embodiment of the present invention, a method of preparing a quaternary data storage device includes depositing an organic film layer on a bottom electrode, the organic film layer containing the organic compound, and depositing a top electrode to form a bottom electrode/organic film layer/top electrode sandwich structure.

In another embodiment of the present invention, a method of preparing the organic compound includes the following steps:

(1) reacting 4,4'-sulfonyldianiline with maleic anhydride to obtain a compound of the following chemical structure:

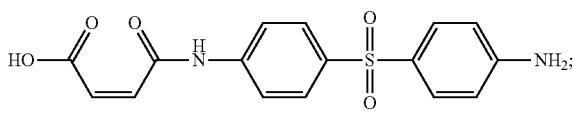 [SMILES: Nc1ccc(S(=O)(=O)c2ccc(NC(=O)/C=C\C(=O)O)cc2)cc1]

(2) converting the compound of step (1) to a diazonium salt of the following chemical structure:

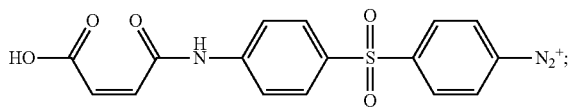

(3) reacting the diazonium salt of step (2) with

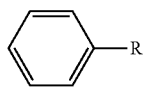

to obtain a compound of the following chemical structure:

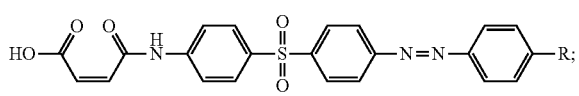

(4) converting the compound of step (3) to a compound of the following chemical structure:

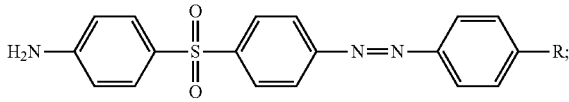

(5) converting the compound of step (4) to a diazonium salt of the following chemical structure:

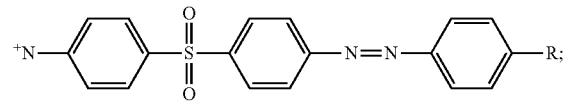

(6) reacting the diazonium salt of step (5) with

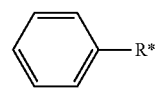

to obtain the organic compound of the following chemical structure:

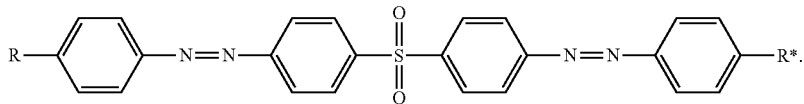

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
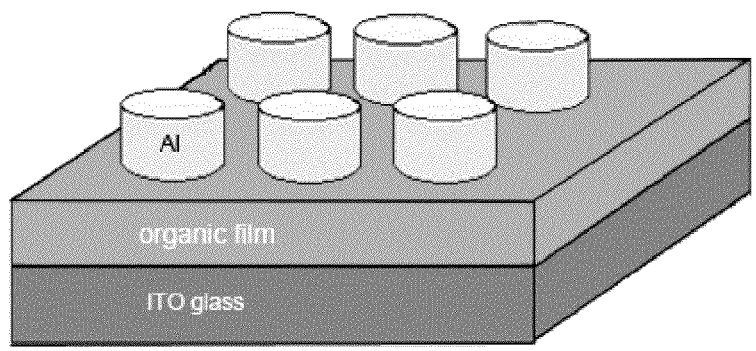
FIG. 1 shows a schematic graph of a quaternary data storage device with a sandwich structure.

Reference will now be made in detail to embodiments of the present invention, example of which is illustrated in the accompanying drawings.

The inventors reported the preparation of an organic molecule of the following formula:

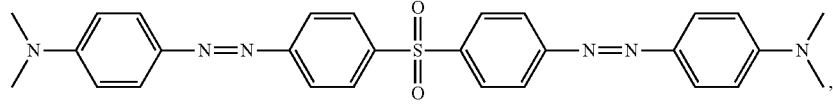

and the fabrication of a data storage device containing this organic molecule. See, H. Li, Q. Xu, N. Li, R. Sun, J. Ge, J. Lu, H. Gu, F. Yan, J. Am. Chem. Soc. 2010, 132, 5542. This memory device has ternary data-storage performance under an external applied voltage.

After further extensive research, the inventors surprisingly found that a data storage device containing an organic compound of the following structure has an unexpected quaternary data-storage performance under an external applied voltage:

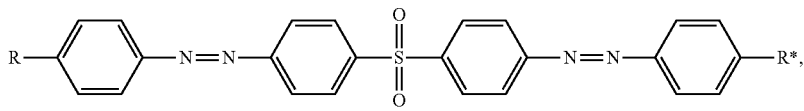

wherein R is different from R*; R and R* are independently hydrogen,

halogen, nitro or methoxyl; and R1 is a C1-C6 alkyl or a phenyl group.

The organic compound can be selected from the group consisting of

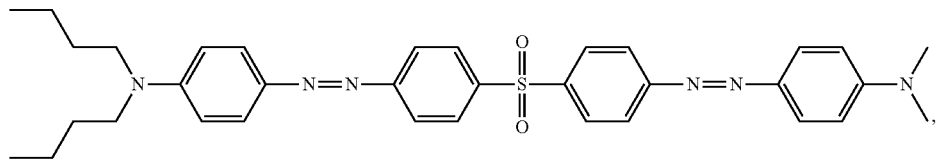

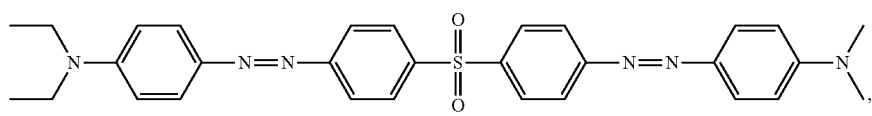

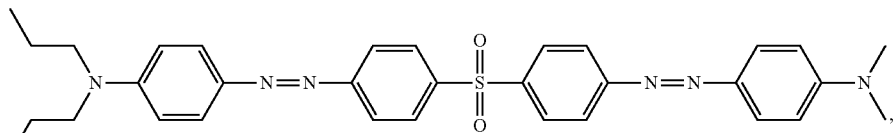

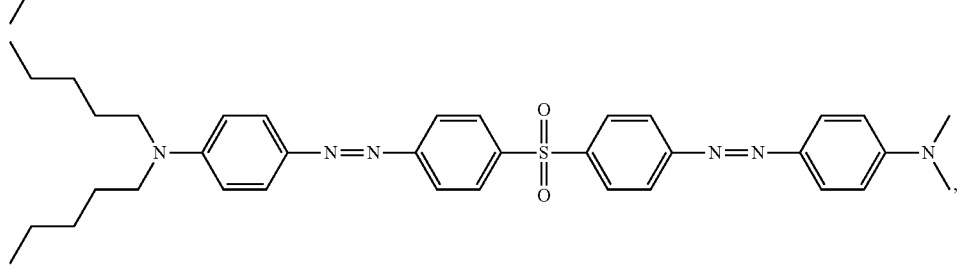

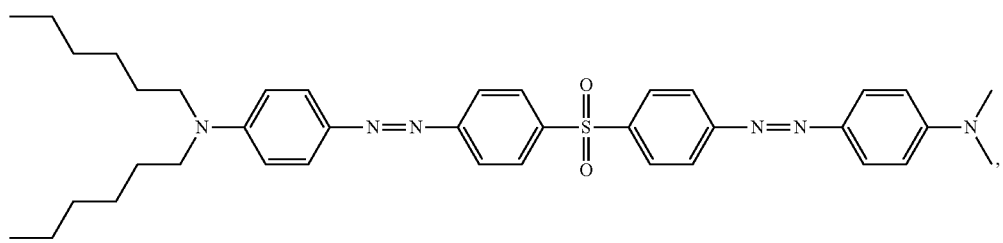

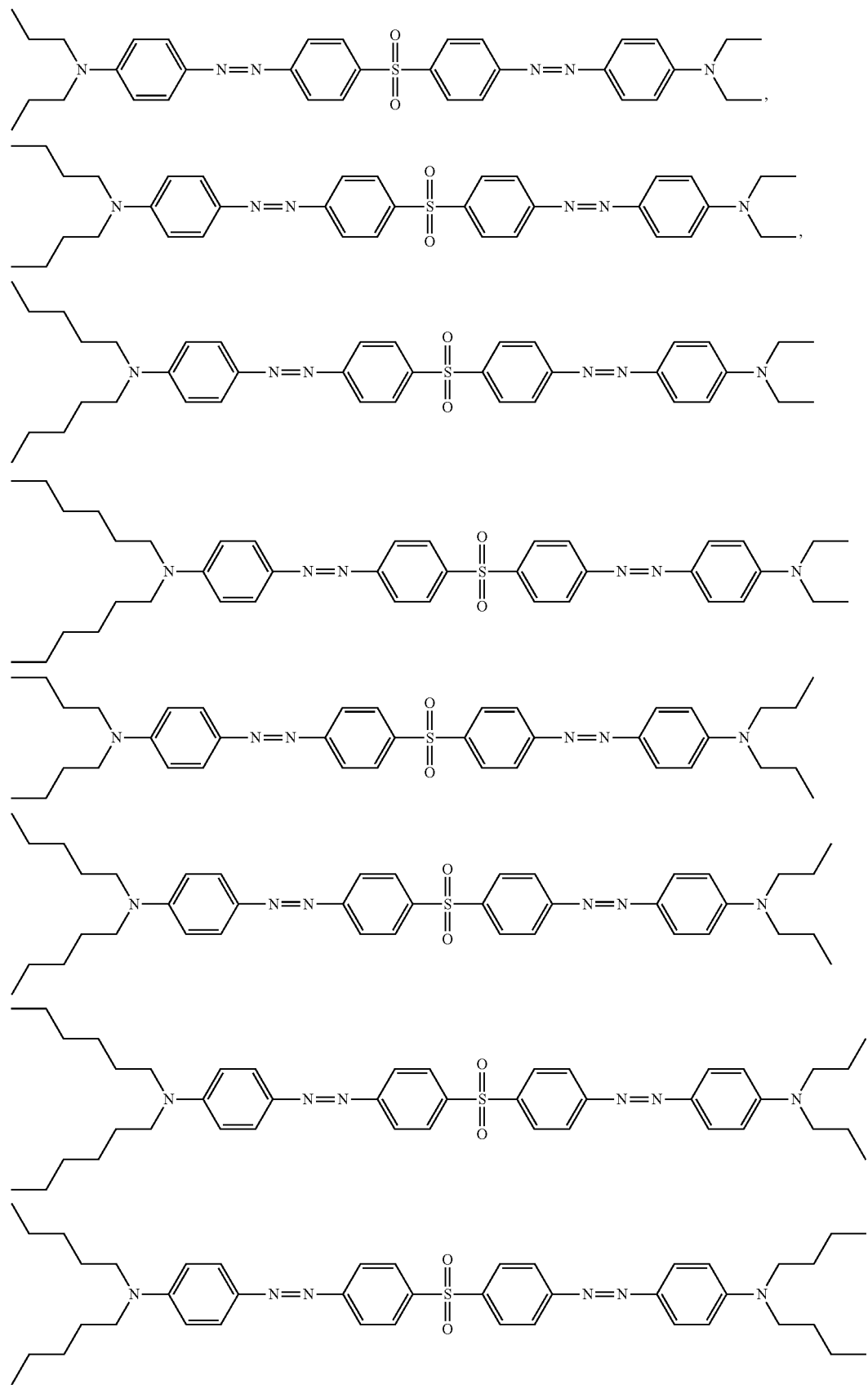

-continued

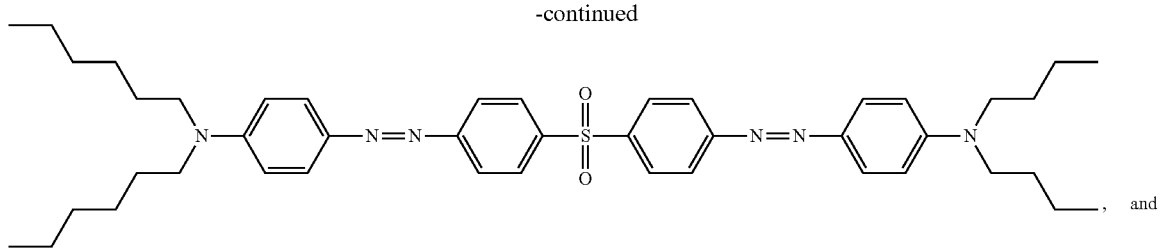
, and

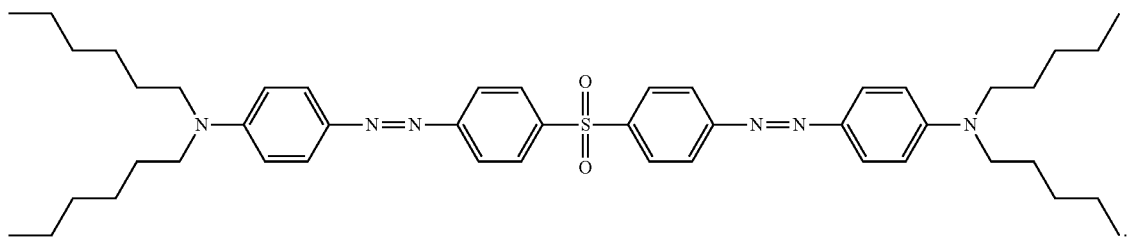
.

This organic compound can be prepared by a method including the following steps:

(1) reacting 4,4'-sulfonyldianiline with maleic anhydride to obtain a compound of the following chemical structure:

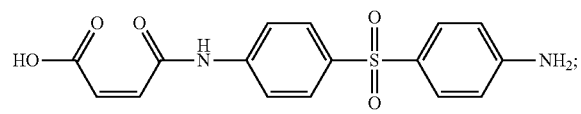 [SMILES: Nc1ccc(S(=O)(=O)c2ccc(NC(=O)/C=C\C(=O)O)cc2)cc1]

(2) converting the compound of step (1) to a diazonium salt of the following chemical structure:

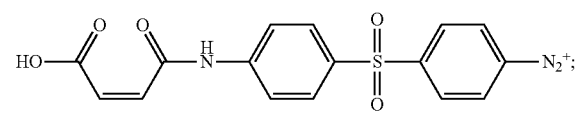

(3) reacting the diazonium salt of step (2) with

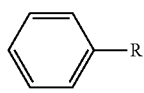

to obtain a compound of the following chemical structure:

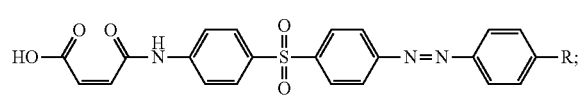

(4) converting the compound of step (3) to a compound of the following chemical structure:

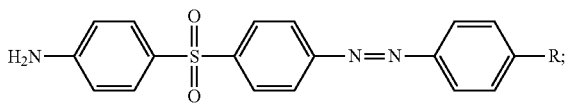

(5) converting the compound of step (4) to a diazonium salt of the following chemical structure:

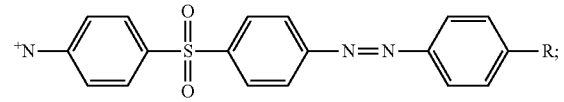

(6) reacting the diazonium salt of step (5) with

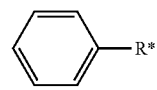

to obtain the organic compound of the following chemical structure:

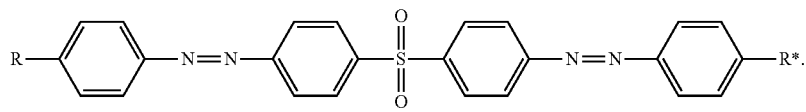

The data storage device containing the organic compound of the chemical structure

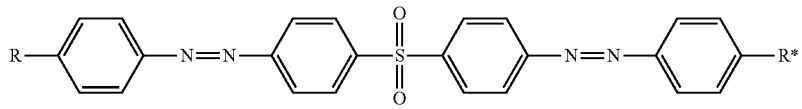

can be prepared in accordance with the method described in H. Li, Q. Xu, N. Li, R. Sun, J. Ge, J. Lu, H. Gu, F. Yan, J. Am. Chem. Soc. 2010, 132, 5542, which is hereby incorporated by reference in its entirety.

Specifically, the data storage device includes a bottom electrode, an electro-active layer, and a top electrode.

The bottom electrode can be selected from indium-tin oxide (ITO), an evaporatable metal, and a conductive polymers. The evaporatable metal can be gold, platinum, silver, aluminum, or copper; and the conductive polymer can be polythiophene or polyaniline.

The electro-active layer includes the organic compound of the chemical structure:

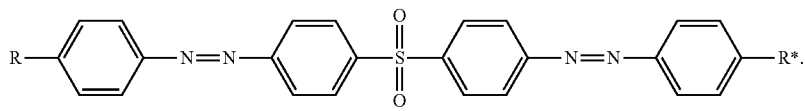

The top electrode is selected from the evaporatable metal and some metal oxides. The evaporatable metal can be gold, platinum, silver, or copper; and the metal oxide can be indium-tin oxide (ITO).

The thickness of the bottom electrode can be 10-300 nm, the thickness of the top electrode can be 20-300 nm, and the thickness of the organic layer can be 20-150 nm.

The active material was first deposited onto the bottom electrode and then the top electrode was deposited onto the organic layer through a shadow mask to construct a bottom electrode/active layer/top electrode sandwich configuration.

The memory performance of the as-fabricated device was then evaluated.

EXPERIMENTAL EXAMPLES

Example 1

The Synthesis of Asymmetric Diazosulfonylbenzene Compounds

General Structure:

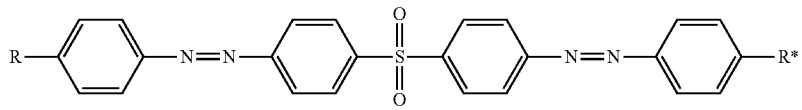

For R1=methyl, R2=butyl, the synthetic processes are shown below:

(1) 4,4'-sulfonyldianiline (1.24 g~4.96 g) and maleic anhydride (0.49 g~1.96 g) were dissolved in acetone (40-60 mL), and after stirring for 4-12 h a lot of white precipitate formed. After filtration, the solid was washed by cool acetone to give white solid (compound 1).

compound 1

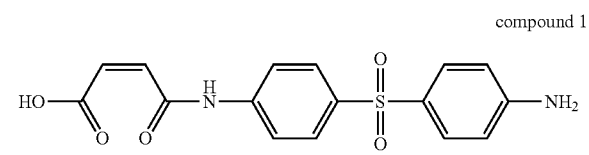 [SMILES: Nc1ccc(S(=O)(=O)c2ccc(NC(=O)/C=C\C(=O)O)cc2)cc1]

(2) Then icy aqueous solution of sodium nitrite was added drop wise into the mixture of compound 1, DMF and 6-12 mol $L^{-1}$ concentrated hydrochloric acid (or sulfuric acid (98%, w %) or fluoroboric acid (40%, w %)) in an ice bath under stirring. The mixture was filtered after stirring for 0.5-2 h at 0-5° C. and the obtained diazonium salt solution was stored in an ice bath.

(3) N,N-dimethylaniline was dissolved in DMF (0.5-2 mol $L^{-1}$) and then added dropwise into the solution of diazonium salt below 10° C. The reaction proceeded for 0.5-2 h, and thereafter the pH value was adjusted to 5-7. The mixture was stirred for another 3-5 h and then poured into a large quantity of water to precipitate solid. After filtration the solid was dried and recrystallized to obtain compound 2.

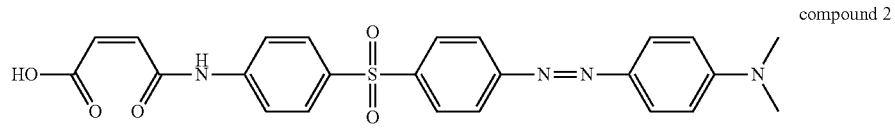 [SMILES: CN(C)c1ccc(N=Nc2ccc(S(=O)(=O)c3ccc(NC(=O)/C=C\C(=O)O)cc3)cc2)cc1]

compound 2

(4) Compound 2 (1 g) was dissolved in methanol and concentrated hydrochloric acid (40-60 mL) was then added followed by refluxing for 1-3 h. Afterward the mixture was poured into a large quantity of water to precipitate solid. After filtration the solid was dried and compound 3 could be obtained through column chromatography.

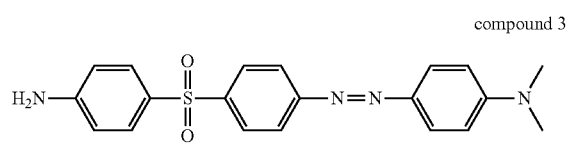 [SMILES: CN(C)c1ccc(N=Nc2ccc(S(=O)(=O)c3ccc(N)cc3)cc2)cc1]

compound 3

(5) Then icy aqueous solution of sodium nitrite was added dropwise into the mixture of compound 3, DMF and concentrated hydrochloric acid (or sulfuric acid or fluoroboric acid at a certain concentration) in an ice bath under stirring. The mixture was filtered after the solution stirring for 0.5-2 h at 0-5° C. and the obtained diazonium salt solution was stored in an ice bath.

(6) N,N-dibutylaniline was dissolved in DMF (0.5-2 mol $L^{-1}$) and was then added dropwise into the solution of diazonium salt below 10° C. The reaction proceeded for 0.5-2 h, and thereafter the pH value was adjusted to 5-7. The mixture was stirred for another 3-5 h and then poured into a large quantity of water to precipitate solid. After filtration the solid was dried and recrystallized to give target molecule A1:

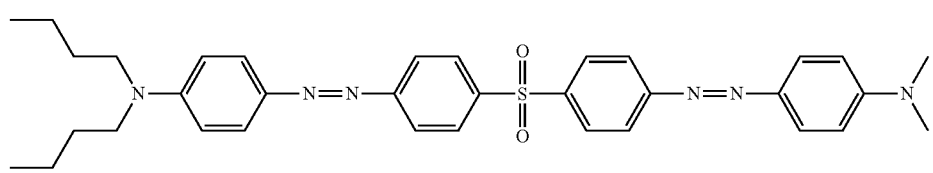

A1

Anal. Calcd for $C_{34}H_{40}N_6O_2S$: C, 68.43; H, 6.76; N, 14.08. Found: C, 68.47; H, 6.72; N, 14.13. $^1$H-NMR (DMSO-$d_6$): δ (ppm)=8.09 (d, 4H), 7.91 (d, 4H), 7.79 (d, 4H), 6.82 (d, 4H), 3.39 (t, 4H), 3.07 (s, 6H), 1.59-1.47 (m, 4H), 1.40-1.30 (m, 4H), 0.91 (t, 6H).

When R1 and R2 are replaced by methyl, ethyl, propyl, butyl, pentyl or hexyl, the reaction processes are similar and the ratios of the reactants are the same. What is different is the N,N-dimethylaniline in step 3 and N,N-dibutylaniline in step 6, which are replaced by N,N-diethylaniline, N,N-dipropylaniline, N,N-dibutylaniline, N,N-dipentylaniline or N,N-dihexylaniline. The obtained target compounds are A2, A3, A4, A5, A6, A7, A8, A9, A10, A11, A12, A13, A14 and A15, respectively. And their molecular structure, element analysis and $^1$H-NMR results are shown below:

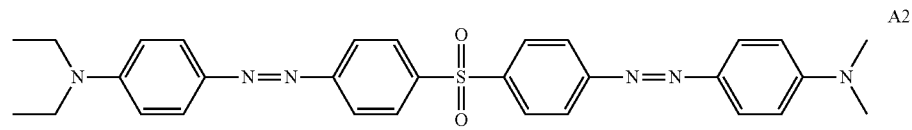 [SMILES: CCN(CC)c1ccc(N=Nc2ccc(S(=O)(=O)c3ccc(N=Nc4ccc(N(C)C)cc4)cc3)cc2)cc1]

A2

Anal. Calcd for $C_{30}H_{32}N_6O_2S$: C, 66.64; H, 5.97; N, 15.54. Found: C, 66.67; H, 6.02; N, 15.51. $^1$H-NMR (DMSO-$d_6$): δ (ppm)=8.08 (d, 4H), 7.90 (d, 4H), 7.78 (d, 4H), 6.81 (d, 4H), 3.54-3.21 (m, 4H), 3.10 (s, 6H), 1.12 (t, 6H).

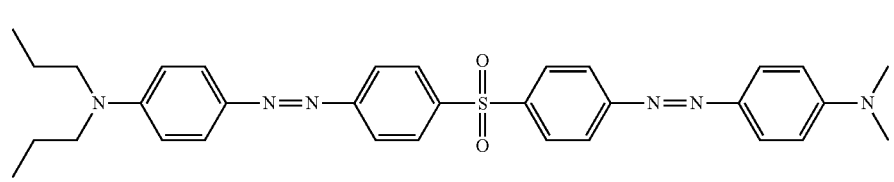

A3

Anal. Calcd for $C_{32}H_{36}N_6O_2S$: C, 67.58; H, 6.38; N, 14.78. Found: C, 67.55, H, 6.39, N, 14.75. $^1$H-NMR (DMSO-$d_6$): δ (ppm)=8.11 (d, 4H), 7.91 (d, 4H), 7.81 (d, 4H), 6.83 (d, 4H), 3.89 (t, 4H), 3.08 (s, 6H), 1.75-1.58 (m, 4H), 0.89 (t, 6H).

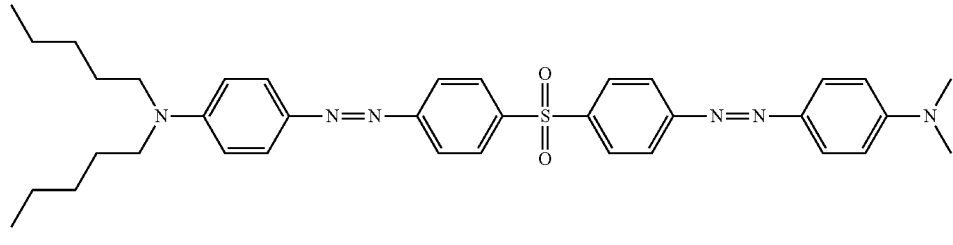

A4

Anal. Calcd for $C_{36}H_{44}N_6O_2S$: C, 69.20; H, 7.10; N, 13.45. Found: C, 69.18, H, 7.11, N, 13.47. $^1$H-NMR (DMSO-$d_6$): δ (ppm)=8.08 (d, 4H), 7.89 (d, 4H), 7.80 (d, 4H), 6.84 (d, 4H), 3.81 (t, 4H), 3.03 (s, 6H), 1.64-1.49 (m, 4H), 1.38-1.27 (m, 8H), 0.95 (t, 6H).

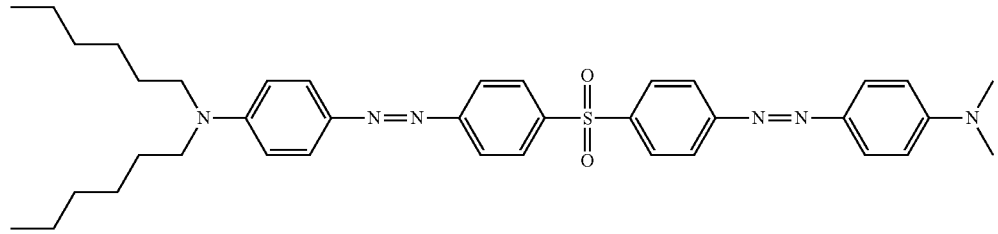

A5

Anal. Calcd for $C_{38}H_{48}N_6O_2S$: C, 69.91; H, 7.41; N, 12.87. Found: C, 69.94, H, 7.44, N, 12.90. $^1$H-NMR (DMSO-$d_6$): δ (ppm)=8.08 (d, 4H), 7.90 (d, 4H), 7.78 (d, 4H), 6.83 (d, 4H), 3.79 (t, 4H), 3.05 (s, 6H), 1.58-1.46 (m, 4H), 1.31-1.29 (m, 12H), 0.91 (t, 6H).

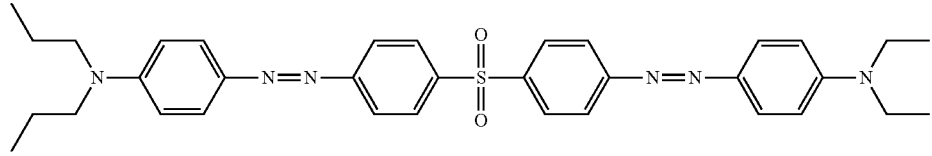

A6

Anal. Calcd for $C_{34}H_{40}N_6O_2S$: C, 68.43; H, 6.76; N, 14.08. Found: C, 68.45; H, 6.73; N, 14.06. $^1$H-NMR (DMSO-$d_6$): δ (ppm)=8.09 (d, 4H), 7.91 (d, 4H), 7.80 (d, 4H), 6.83 (d, 4H), 3.83 (t, 4H), 3.43 (m, 4H), 1.59 (m, 4H), 1.17 (t, 6H), 0.93 (t, 6H).

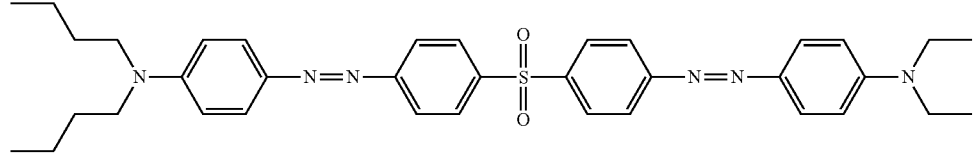

A7

Anal. Calcd for $C_{36}H_{44}N_6O_2S$: C, 69.20; H, 7.10; N, 13.45. Found: C, 69.23; H, 7.11; N, 13.47. $^1$H-NMR (DMSO-$d_6$): δ (ppm)=8.06 (d, 4H), 7.91 (d, 4H), 7.79 (d, 4H), 6.82 (d, 4H), 3.74 (t, 4H), 3.45-3.33 (m, 4H), 1.49-1.40 (m, 4H), 1.35-1.26 (m, 4H), 1.13 (t, 6H), 0.87 (t, 6H).

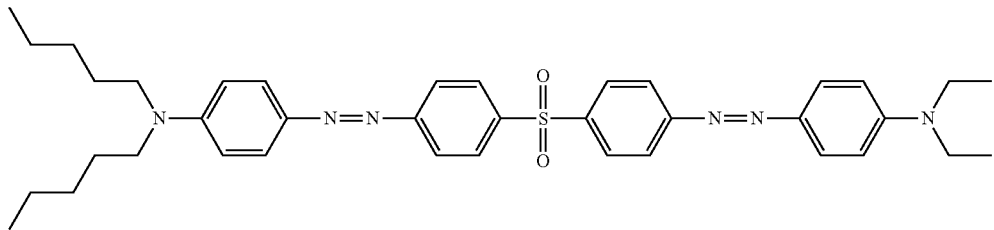

A8

Anal. Calcd for C$_{38}$H$_{48}$N$_6$O$_2$S: C, 69.91; H, 7.41; N, 12.87. Found: C, 69.93; H, 7.43; N, 12.91. $^1$H-NMR (DMSO-d$_6$): δ (ppm)=8.07 (d, 4H), 7.92 (d, 4H), 7.80 (d, 4H), 6.83 (d, 4H), 3.77 (t, 4H), 3.49-3.42 (m, 4H), 1.61-1.52 (m, 4H), 1.38-1.29 (m, 8H), 1.17 (t, 6H), 0.93 (t, 6H).

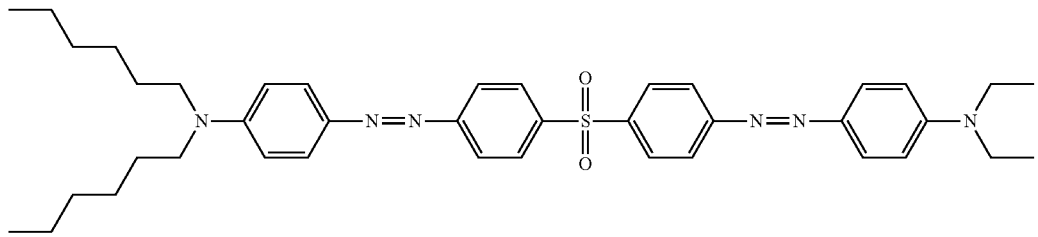

A9

Anal. Calcd for C$_{40}$H$_{52}$N$_6$O$_2$S: C, 70.55; H, 7.70; N, 12.34. Found: C, 70.57; H, 7.68; N, 12.36. $^1$H-NMR (DMSO-d$_6$): δ (ppm)=8.12 (d, 4H), 7.93 (d, 4H), 7.80 (d, 4H), 6.85 (d, 4H), 3.79 (t, 4H), 3.45-3.36 (m, 4H), 1.50-1.44 (m, 4H), 1.28-1.20 (m, 12H), 1.13 (t, 6H), 0.94 (t, 6H).

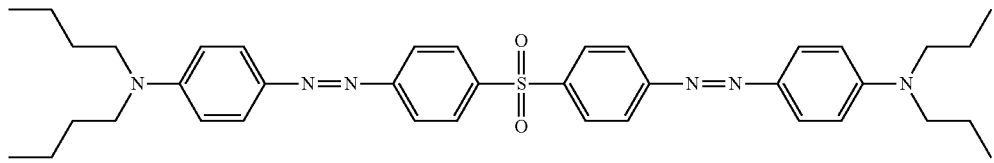

A10

Anal. Calcd for C$_{38}$H$_{48}$N$_6$O$_2$S: C, 69.91; H, 7.41; N, 12.87. Found: C, 69.93; H, 7.44; N, 12.89. $^1$H-NMR (DMSO-d$_6$): δ (ppm)=8.07 (d, 4H), 7.89 (d, 4H), 7.82 (d, 4H), 6.83 (d, 4H), 3.75 (t, 8H), 1.64-1.57 (m, 4H), 1.53-1.46 (m, 4H), 1.33-1.28 (m, 4H), 1.01 (t, 12H).

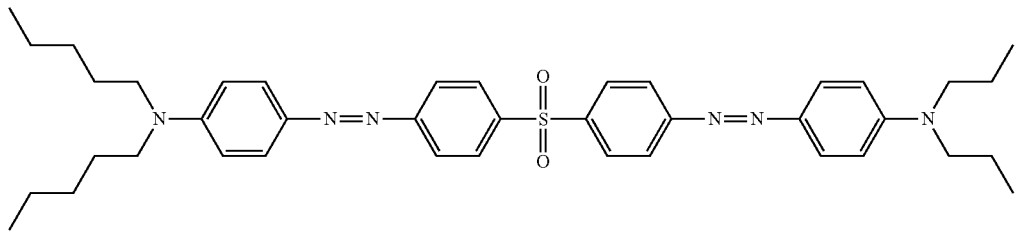

A11

Anal. Calcd for C$_{40}$H$_{52}$N$_6$O$_2$S: C, 70.55; H, 7.70; N, 12.34. Found: C, 70.57; H, 7.75; N, 12.33. $^1$H-NMR (DMSO-d$_6$): δ (ppm)=8.10 (d, 4H), 7.92 (d, 4H), 7.81 (d, 4H), 6.84 (d, 4H), 3.75 (t, 8H), 1.66-1.61 (m, 4H), 1.55-1.49 (m, 4H), 1.37-1.32 (m, 4H), 1.30-1.26 (m, 4H), 1.04 (t, 12H).

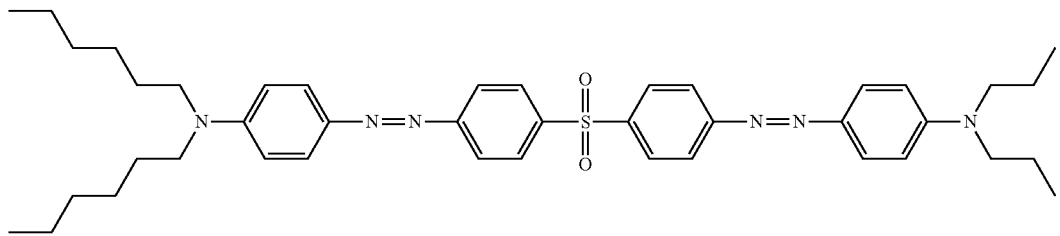

A12

Anal. Calcd for $C_{42}H_{56}N_6O_2S$: C, 71.15; H, 7.96; N, 11.85. Found: C, 71.18; H, 7.93; N, 11.88. $^1$H-NMR (DMSO-$d_6$): δ (ppm)=8.10 (d, 4H), 7.93 (d, 4H), 7.79 (d, 4H), 6.84 (d, 4H), 3.77 (t, 8H), 1.63-1.58 (m, 4H), 1.56-1.51 (m, 4H), 1.36-1.32 (m, 4H), 1.29-1.25 (m, 8H), 0.89 (t, 12H).

Anal. Calcd for $C_{46}H_{64}N_6O_2S$: C, 72.21; H, 8.43; N, 10.98. Found: C, 72.24; H, 8.44; N, 10.97. $^1$H-NMR (DMSO-$d_6$): δ (ppm)=8.09 (d, 4H), 7.90 (d, 4H), 7.81 (d, 4H), 6.83 (d, 4H), 3.72 (t, 8H), 1.51-1.45 (m, 8H), 1.29-1.20 (m, 20H), 0.92 (t, 12H).

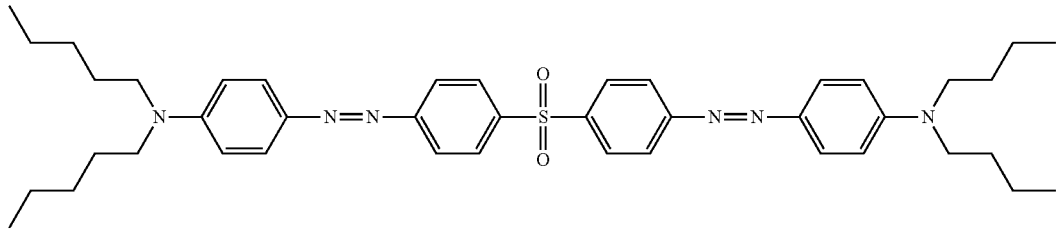

A13

Anal. Calcd for $C_{42}H_{56}N_6O_2S$: C, 71.15; H, 7.96; N, 11.85. Found: C, 71.12; H, 7.97; N, 11.84. $^1$H-NMR (DMSO-$d_6$): δ (ppm)=8.11 (d, 4H), 7.93 (d, 4H), 7.82 (d, 4H), 6.85 (d, 4H), 3.76 (t, 8H), 1.53-1.48 (m, 8H), 1.32-1.27 (m, 12H), 0.97 (t, 12H).

Example 2

Compound A1 was selected as the electroactive material sandwiched between the top and bottom electrode to construct the memory device. Before deposition of the organic

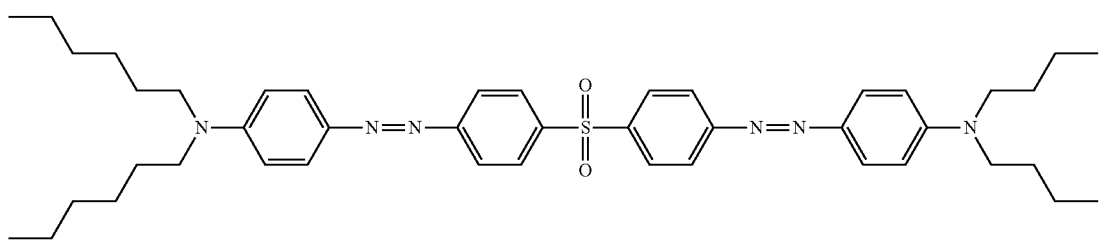

A14

Anal. Calcd for $C_{44}H_{60}N_6O_2S$: C, 71.70; H, 8.21; N, 11.40. Found: C, 71.69; H, 8.22; N, 11.37. $^1$H-NMR (DMSO-$d_6$): δ (ppm)=8.07 (d, 4H), 7.88 (d, 4H), 7.78 (d, 4H), 6.81 (d, 4H), 3.71 (t, 8H), 1.50-1.44 (m, 8H), 1.29-1.20 (m, 16H), 0.87 (t, 12H).

layer, the ITO glass was precleaned by ultrasonication with water, acetone, and 2-propanol, each for 5-30 min. Compound A1 (20-30 mg) was placed in quartz crucible and was then moved into the molybdenum boat. The evaporation of the organic material wasn't launched until the pressure inside

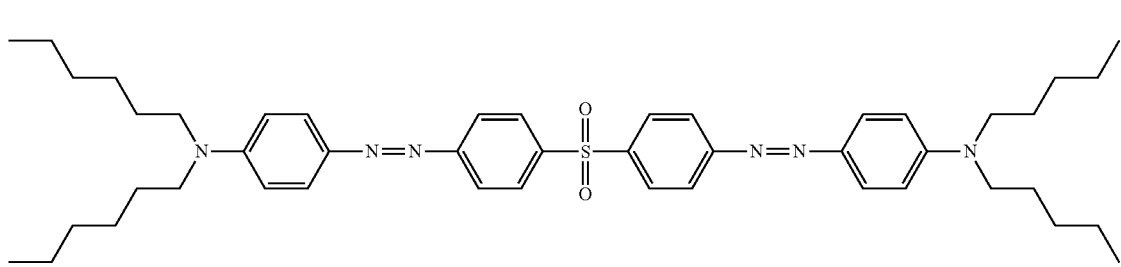

Figure 2:
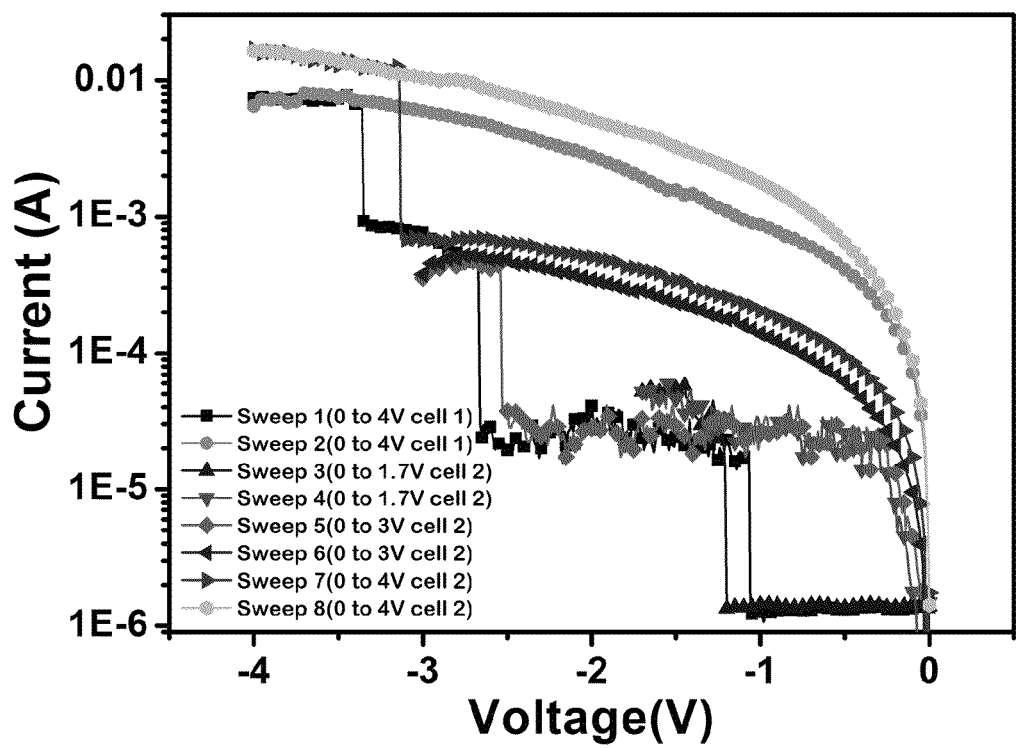
FIG. 2 shows the current-voltage characteristics of the quaternary data storage device.

A15 was lower than $3\times10^{-3}$ Pa. The thickness of the organic layer was controlled between 60 and 100 nm by the film thickness monitor. After the successful deposition of the organic layer, a porous metal mask (pore radius=0.1 mm) was fixed onto the organic film. Thereafter aluminum hanging on the tungsten filaments was evaporated onto the film when the pressure inside was lower than $8\times10^{-3}$ Pa to form top electrodes. The scheme of the device is shown in FIG. 2.

Figure 3:
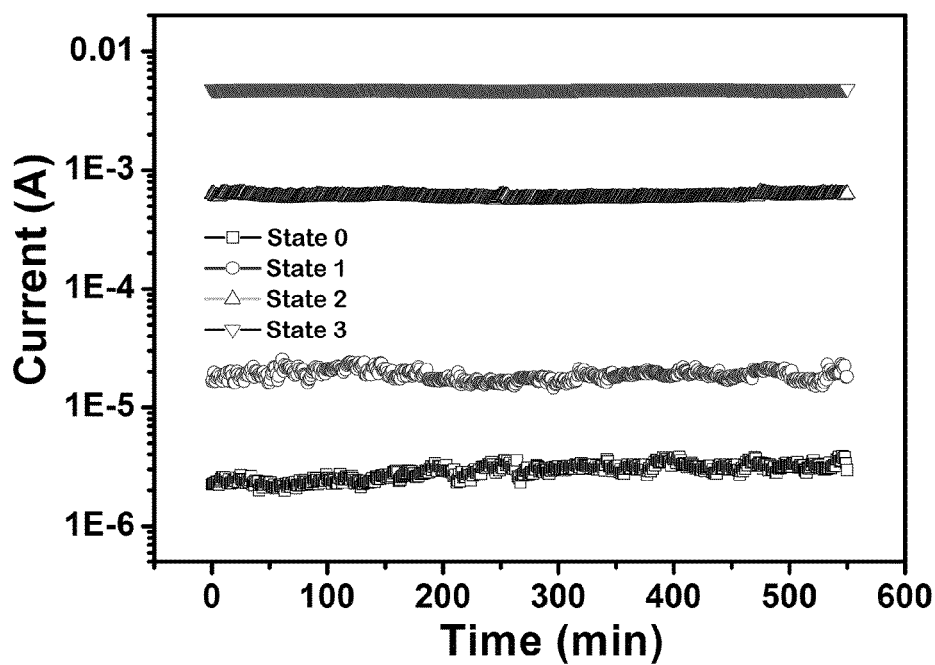
FIG. 3 shows the current stability of the quaternary data storage device under a constant stress.
Figure 4:
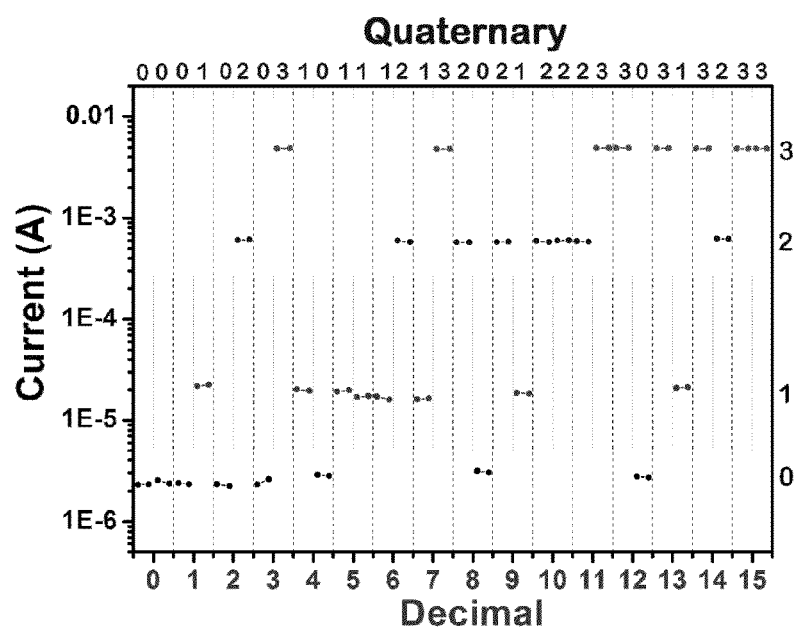
FIG. 4 shows quaternary data storage performance of the data storage device.

FIG. 3 shows the current-voltage curve of the as-fabricated device. When a bias from 0 to −4 V was applied to a cell in the device, three abrupt increase of the current through the device was observed around −1.14 V, −2.60 V and −3.38 V respectively, suggesting that there are four distinct current states (OFF, ON1, ON2 and ON3) for the measured cell (sweep1 in FIG. 2). In order to demonstrate that these observed four states were all stable and this phenomenon was not by coincidence, we selected another cell to perform the reproducibility and stability test. In the beginning, a constant voltage of −1 V was added to evaluate the stability of the OFF state, and the corresponding I-t curve was denoted as line A in FIG. 3. A short period of only 600 s was tested due to the limit of the data storage capability of the instrument. And no obvious degradation of the OFF current was observed. Then a subsequent sweep from 0 to −1.7 V was applied to the cell, similar to the first cell, an abrupt increase in current was observed around −1.2 V, indicating the transition from the OFF state to the ON1 state (sweep3 in FIG. 2). Afterward the stability of the ON1 state was tested with a constant voltage of −1 V (line B in FIG. 3). Then the voltage was swept from 0 to −3V, and a transition from ON1 to ON2 state was observed around −2.55 V. Thereafter the stability of the ON2 state was tested with a constant voltage of −1 V (line C in FIG. 3). Lastly the voltage was swept from 0 to −4V, and a transition from ON2 to ON3 state was observed around −3.2 V. Then the stability of the ON3 state was tested with a constant voltage of −1 V (line D in FIG. 3). The reproducibility and stability of the four distinct states were further confirmed by measurement of other cells in the device. The OFF, ON1, ON2 and ON3 states of the device can be encoded as "0", "1", "2" and "3" generally adopted in data storage. And further 32 cells were selected to be programmed to different states with different on-switching voltages and then a constant voltage of −1 V was applied to read the current level. FIG. 4 was obtained via combination of two states, which demonstrates the feasibility for the application of quaternary data storage. The programmed states cannot be reprogrammed to the OFF state, suggesting the WORM-type data-storage behavior.

In this invention, the bottom electrode is not confined to the indium-tin oxide (ITO) glass. Various evaporatable metals including gold, platinum, silver, aluminum and copper and conductive polymers including polythiophene and polyaniline are also involved. And the top electrode is not limited to aluminum. Evaporatable metals including gold, platinum, aluminum and copper and metal oxide like indium-tin oxide (ITO) are involved.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An organic compound of the following chemical structure:

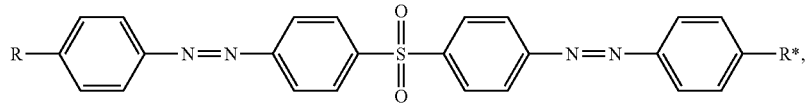

wherein R is different from R*; R and R* are independently hydrogen,

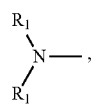

halogen, nitro or methoxyl; and R1 is a C1-C6 alkyl or a phenyl group.

2. The organic compound of claim 1, wherein the organic compound is selected from the group consisting of

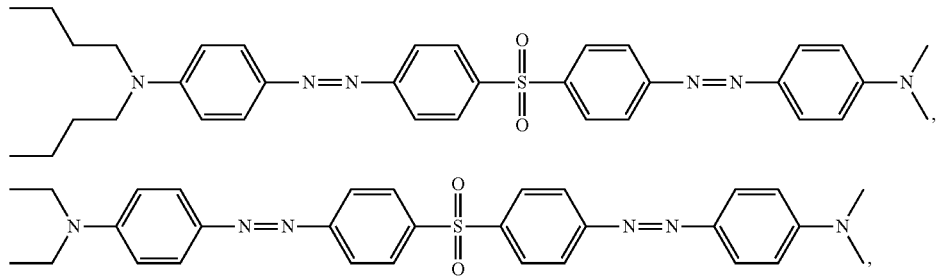

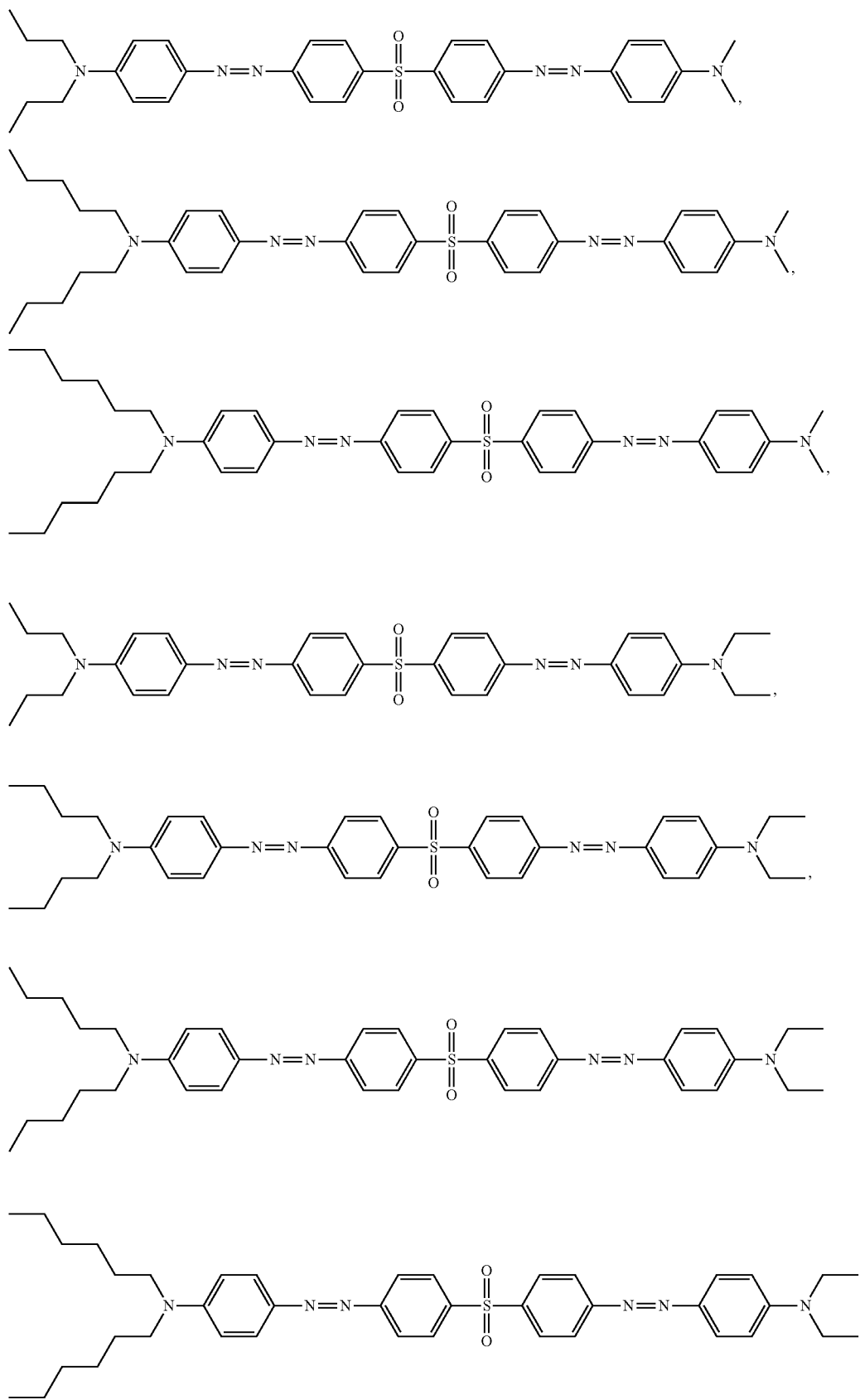

-continued

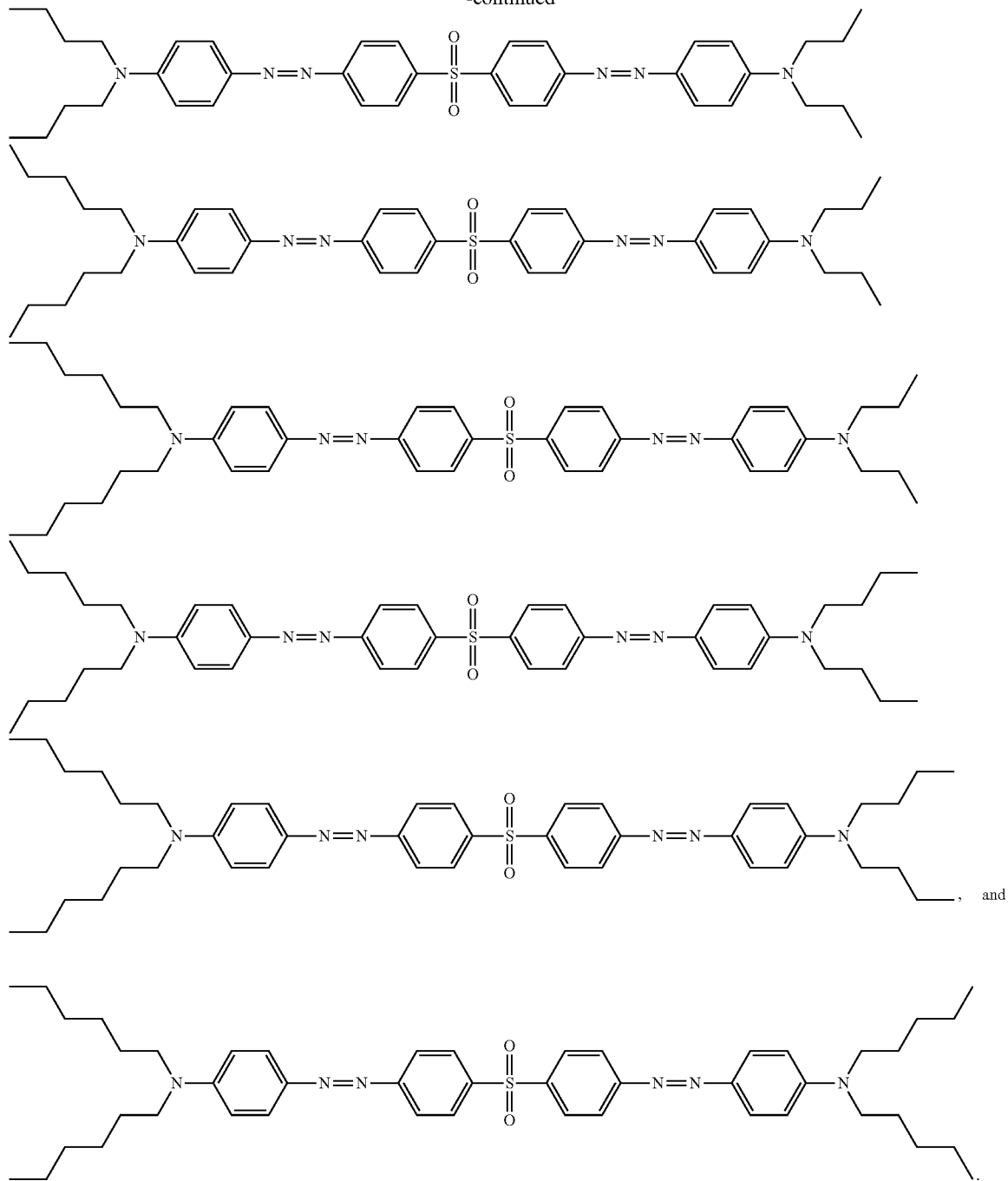

, and

3. A quaternary data storage device comprising:
a bottom electrode,
a top electrode, and
an organic film layer sandwiched between the bottom electrode and the top electrode, the organic film layer including the organic compound of claim 1.

4. The quaternary data storage device of claim 3, wherein the thickness of the bottom electrode is 10-300 nm, the thickness of the top electrode is 20-300 nm, and the thickness of the organic layer is 20-150 nm.

5. The quaternary data storage device of claim 3, wherein the bottom electrode is selected from the group consisting of indium-tin oxide (ITO), an evaporatable metal, and a conductive polymer.

6. The quaternary data storage device of claim 5, wherein the evaporatable metal is gold, platinum, silver, aluminum, or copper; and the conductive polymer is polythiophene or polyaniline.

7. The quaternary data storage device of claim 3, wherein the top electrode is selected from the group consisting of an evaporatable metal and a metal oxide.

8. The quaternary data storage device of claim 7, wherein the evaporatable metal is gold, platinum, silver, or copper; and the metal oxide is indium-tin oxide (ITO).

9. A method of preparing a quaternary data storage device comprising
depositing an organic film layer on a bottom electrode, the organic film layer including the organic compound of claim 1, and
depositing a top electrode to form a bottom electrode/organic film layer/top electrode sandwich structure.

10. The method of claim 9, wherein the thickness of the bottom electrode is 10-300 nm, the thickness of the top electrode is 20-300 nm, and the thickness of the organic layer is 20-150 nm.

11. The method of claim 9, wherein the bottom electrode is selected from the group consisting of indium-tin oxide (ITO), an evaporatable metal, and a conductive polymer.

12. The method of claim 11, wherein the evaporatable metal is gold, platinum, silver, aluminum, or copper; and the conductive polymer is polythiophene or polyaniline.

13. The method of claim 9, wherein the top electrode is selected from the group consisting of an evaporatable metal and a metal oxide.

14. The method of claim 13, wherein the evaporatable metal is gold, platinum, silver, or copper; and the metal oxide is indium-tin oxide (ITO).

15. A method of preparing an organic compound of the following chemical structure:

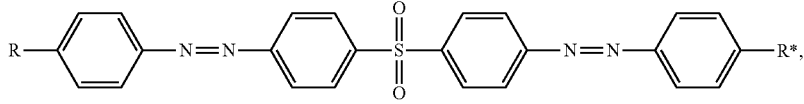

comprising the following steps:
(1) reacting 4,4'-sulfonyldianiline with maleic anhydride to obtain a compound of the following chemical structure:

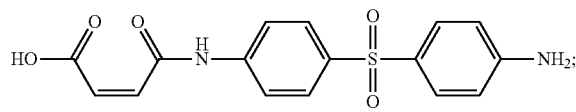

(2) converting the compound of step (1) to a diazonium salt of the following chemical structure:

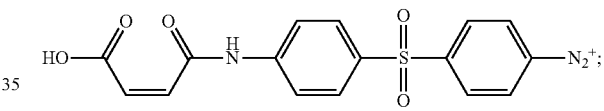

(3) reacting the diazonium salt of step (2) with

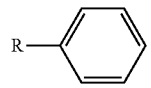

to obtain a compound of the following chemical structure:

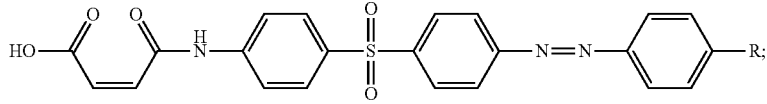

(4) converting the compound of step (3) to a compound of the following chemical structure:

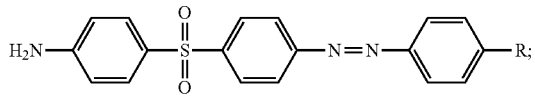

(5) converting the compound of step (4) to a diazonium salt of the following chemical structure:

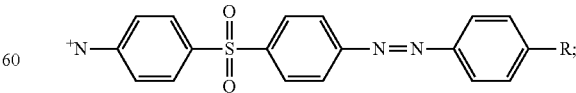

(6) reacting the diazonium salt of step (5) with

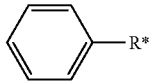

to obtain the organic compound of the following chemical structure
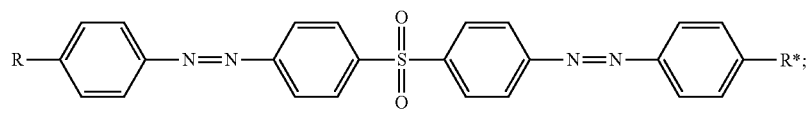
wherein R is different from R*; R and R* are independently hydrogen,
halogen, nitro or methoxyl; and R1 is a C1-C6 alkyl or a phenyl group.
16. The organic compound prepared according to claim 15 is selected from the group consisting of
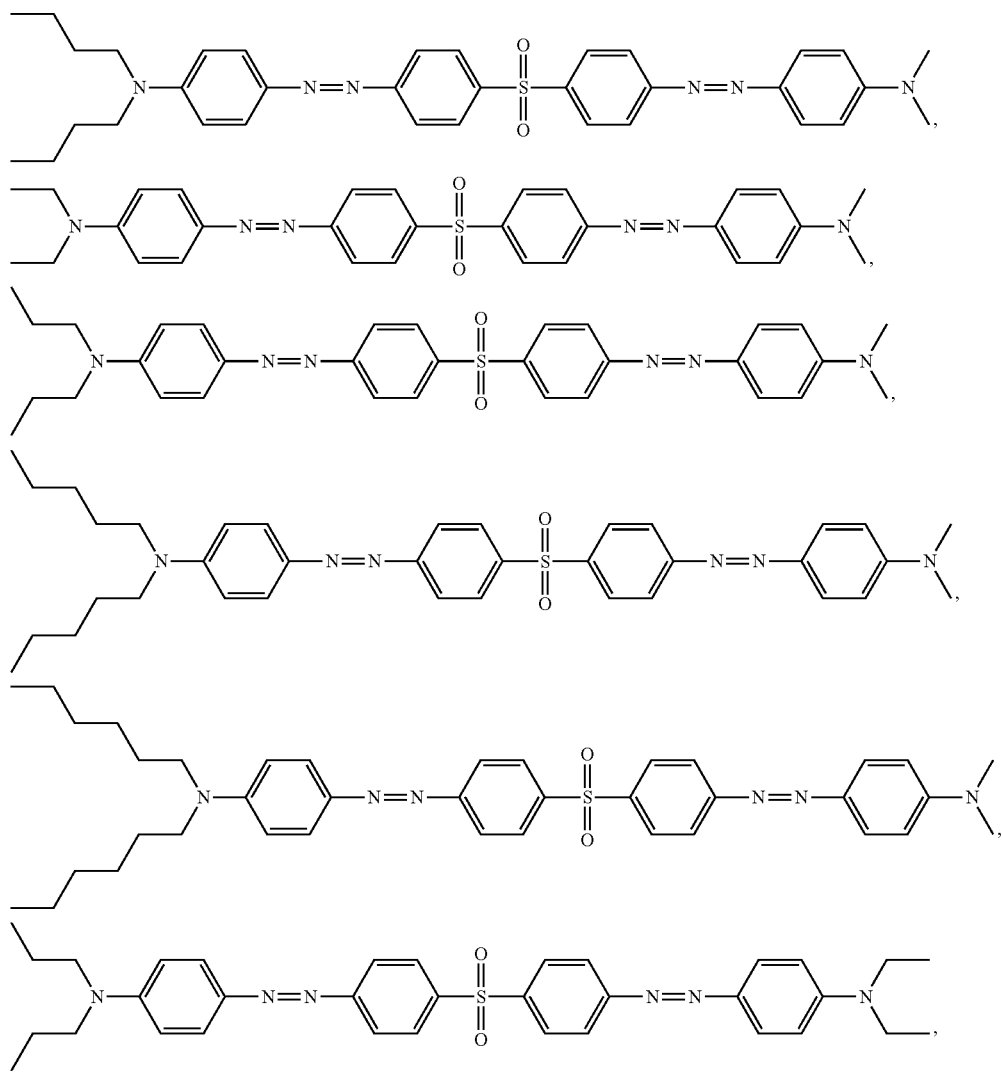

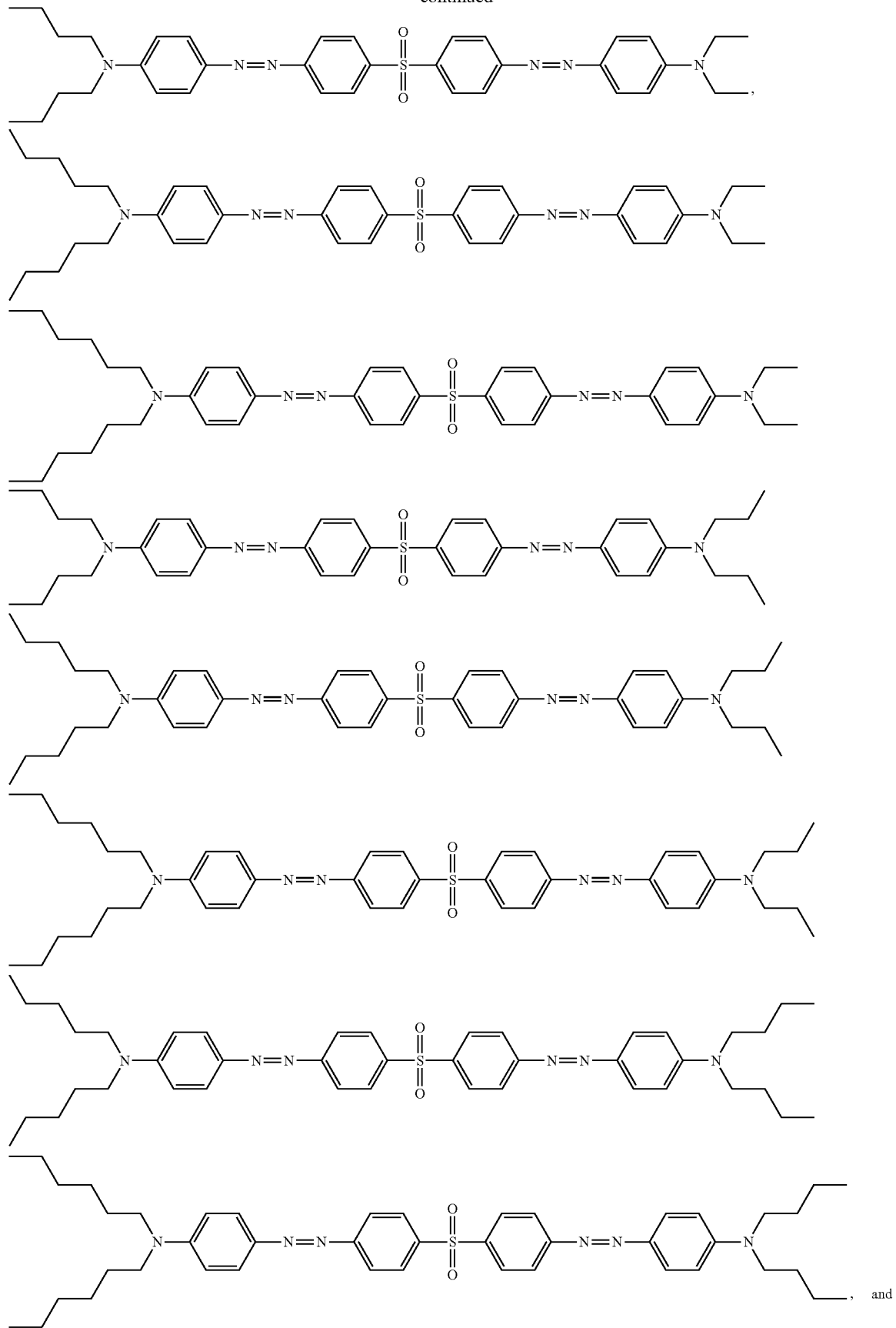

-continued
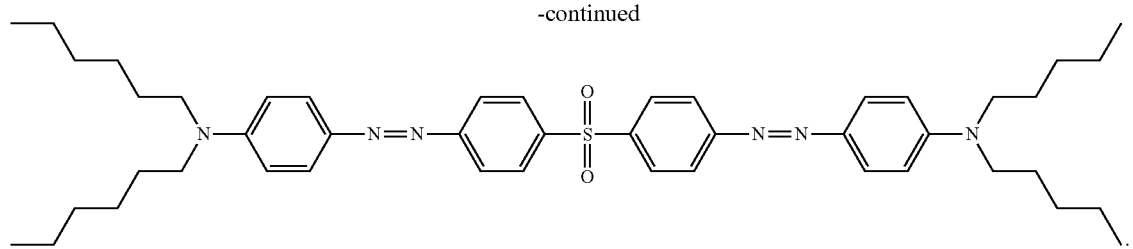
* * * * *